United States Patent
Baumann et al.

(10) Patent No.: US 9,549,664 B2
(45) Date of Patent: Jan. 24, 2017

(54) MEDICAL INSTRUMENT WITH A WINDOW

(75) Inventors: Harald Baumann, Tuttlingen (DE); Elmar Teichtmann, Heilbronn (DE)

(73) Assignee: Karl Storz GmbH & Co. KG, Tuttlingen (DE)

(*) Notice: Subject to any disclaimer, the term of this patent is extended or adjusted under 35 U.S.C. 154(b) by 536 days.

(21) Appl. No.: 13/151,022

(22) Filed: Jun. 1, 2011

(65) Prior Publication Data

US 2012/0029276 A1  Feb. 2, 2012

(30) Foreign Application Priority Data

Jun. 1, 2010  (DE) .................. 10 2010 022 432

(51) Int. Cl.
*A61B 1/04* (2006.01)
*A61B 1/06* (2006.01)
*A61B 1/00* (2006.01)
*G02B 23/24* (2006.01)

(52) U.S. Cl.
CPC ......... *A61B 1/00163* (2013.01); *A61B 1/0011* (2013.01); *A61B 1/00064* (2013.01); *G02B 23/2423* (2013.01); *Y10T 29/49826* (2015.01)

(58) Field of Classification Search
USPC ........ 600/109–113, 127–130, 133, 160–181; 362/574; 385/117, 119; 29/428
See application file for complete search history.

(56) References Cited

U.S. PATENT DOCUMENTS

| | | | |
|---|---|---|---|
| 4,669,818 A | 6/1987 | Myer | |
| 4,779,613 A * | 10/1988 | Hashiguchi et al. | 600/169 |
| 6,547,721 B1 * | 4/2003 | Higuma et al. | 600/133 |
| 2002/0128539 A1 | 9/2002 | Higuma et al. | 600/133 |
| 2004/0210108 A1 * | 10/2004 | Shimizu et al. | 600/112 |
| 2006/0004259 A1 * | 1/2006 | Ross et al. | 600/161 |
| 2006/0235274 A1 * | 10/2006 | Forster et al. | 600/133 |
| 2006/0252996 A1 * | 11/2006 | Goldfain et al. | 600/200 |
| 2006/0276691 A1 * | 12/2006 | Forkey et al. | 600/172 |

FOREIGN PATENT DOCUMENTS

| | | | |
|---|---|---|---|
| DE | 9412590 U1 | 10/1994 | |
| DE | 19644729 A1 | 1/1998 | |
| DE | 19836285 C1 | 10/1999 | |
| DE | 19941320 A1 | 3/2000 | |
| EP | 2105777 A1 | 9/2009 | |
| JP | 2005234239 A * | 9/2005 | ............... A61B 1/00 |

OTHER PUBLICATIONS

German Search Report; Application No. DE 10 2010 022 432.4; Oct. 7, 2010; 4 pages.
European Search Report; Application No. EP 11 16 7768; Issued: Aug. 9, 2011; 6 pages.

* cited by examiner

*Primary Examiner* — Ryan Henderson
(74) *Attorney, Agent, or Firm* — Whitmyer IP Group LLC

(57) ABSTRACT

A medical instrument includes a housing with an aperture, a window component that comprises a transparent material and closes off the aperture, and a thin-walled area that surrounds the aperture.

18 Claims, 2 Drawing Sheets

MEDICAL INSTRUMENT WITH A WINDOW

CROSS-REFERENCE TO RELATED APPLICATIONS

The present application claims priority of German patent application No. 10 2010 022 432.4 filed on Jun. 1, 2010.

FIELD OF THE INVENTION

The present invention relates to a medical instrument with a window that closes off an aperture, and also to a method for producing a medical instrument. The medical instrument is, in particular, an endoscope.

BACKGROUND OF THE INVENTION

Medical instruments must be cleaned and sterilized before every use. Sterilization is performed as a rule by autoclaving, that is, in a pure steam atmosphere at high pressure and at temperatures well over 100 degrees Celsius. Penetration of steam into an endoscope or other optical medical instrument would have disadvantageous consequences for the instrument's optical properties.

As a rule, therefore, optical medical instruments comprise hermetically sealed and insulated apertures through which light must pass in and out, for example on the distal and proximal ends of an endoscope, and which are closed off by window components made of a transparent material. Many window components are made of sapphire, which is characterized by great hardness and chemical resistance. To form a hermetically sealed connection, the edge of a sapphire window can be joined with the housing by soldering. Sapphire, however, is (single-axis) streaming-birefringent and therefore is not unconditionally suited for diagnostic methods that use polarized light.

Glasses are not birefringent but are frequently disturbed by thermally induced mechanical stresses immediately upon cooling after the soldering procedure. An additional problem consists in the fact that a few conventional glass solders are not biocompatible with advantageous mechanical properties relating to manufacturing. Therefore these glass solders cannot automatically be used for medical instruments that come into contact with the human body.

SUMMARY OF THE INVENTION

It is an object of the present invention to provide an improved medical instrument with a window component, and an improved method for producing a medical instrument with a window component.

This object is achieved through the contents of the independent claims.

Refinements are indicated in the dependent claims.

Embodiments of the present invention are based on the idea of providing a lip on the edge of an aperture of a medical instrument, the inner edge of said lip being contiguous with the edge of the window component. Said lip then divides, for example, a soldering on its interior, which ensures hermetical insulation, from a cement on its outside, which ensures biocompatibility.

Further embodiments of the present invention are based on the idea of configuring, on a medical instrument with a window component, an area that surrounds the window component as a solid-state joint. Mechanical stresses can be reduced in the solid-state joint so that they can no longer endanger the window component. Therefore, materials can be used for the window component that conventionally are disturbed by thermally conditioned mechanical stresses and therefore cannot be used.

A medical instrument includes a housing with an aperture, a window component, which comprises a transparent material and closes off the aperture, and a thin-walled portion that surrounds the aperture.

The thin-walled portion of the housing is thinner, and in particular significantly thinner, than other areas of the housing. The wall thickness of the housing, in the thin-walled area for example, is equal to only one-third, one-fifth or one-tenth of the average wall thickness of the housing.

In several ways described hereinafter, the thin-walled portion can reduce the mechanical stress on the window component and/or simplify the manufacture of the medical instrument.

In a medical instrument as described here, the thin-walled portion can comprise a lip with an edge that is contiguous with an edge surface of the window component.

In particular with the characteristics described hereinafter, the window component can close and hermetically insulate the aperture in the housing. The lip, in particular, lies in a plane or essentially in a plane whose normal is parallel or essentially parallel to the longitudinal axis of the medical instrument. The lip is thinner, or comprises a lesser wall thickness, than other portions of the housing. In particular, the lip has a thickness of less than 0.5 mm or less than 0.3 mm. The lip is, in particular, configured as a single piece with the housing. The lip extends, in particular, along the entire edge of the aperture. All local surface normals of the edge surface are, in particular, in a plane in which the aperture lies. The edge surface of the window component with which the edge of the lip is contiguous is, in particular, the mantle surface of a circular or other type of cylinder.

Depending on its configuration, the lip can, in alternation or simultaneously, fulfill several functions. In particular with a thin-walled configuration of the lip, said lip can be suited to absorb mechanical stresses and thus to reduce the mechanical stresses to which the window component is exposed, for example in cooling after a soldering procedure. In particular when the radially inside edge of the lip is contiguous not with an edge of the edge surface of the window component but with a center portion of the edge surface, the lip can be suited to insulate soldering on its inside from cement on its outside. The inside of the lip is understood to refer to the side of the lip facing the internal space of the housing. The outside of the lip refers to the side of the lip facing the surrounding of the housing.

As already mentioned, in a medical instrument as described here, soldering inside the lip can cohesively bind a frame around the aperture and the edge surface of the window component.

As also mentioned above, in a medical instrument as described here, a cement outside the lip can cohesively bind the frame around the aperture and the edge surface of the window component.

The frame is formed in particular by the housing, or is a one-piece or integral component of the housing. The solder, in particular, is not only cohesively bound with the frame and the edge surface of the window component, but also with the inside of the lip, or at least borders on said inside of the lip.

A cohesive binding of the frame and the edge surface of the window component by means of soldering can ensure hermetic insulation of the joining site. The lip can avoid direct contact between the solder and the surrounding of the medical instrument. When the solder is not biocompatible, this can make it possible to use the medical instrument in the human body.

An additional improvement is possible in that the cement is simultaneously provided outside the lip. Said cement can likewise contribute to the spatial separation between the solder and the surrounding of the medical instrument. In case of simultaneous use of a solder inside the lip and of a cement outside the lip, the lip can prevent or at least restrict diffusion of components of the solder into the cement or vice versa. Thereby several combinations of solders and cements, which each comprise advantageous properties in their own right, become possible only because a reciprocal destruction is prevented or at least markedly slowed.

In a medical instrument as described here, the thin-walled portion of the housing can include a solid-state joint.

The portion of the housing configured as a solid-state joint is in particular similar to the shape of the edge of the window component or in some cases of the frame and/or is at a constant distance from the edge of the window component or in some cases from the frame. The solid-state joint comprises a markedly lesser wall thickness in comparison with other portions of the housing and thus a markedly greater elasticity. In particular, the wall thickness in the area of the solid-state joint amounts at most to one-third or at most one-fifth or at most one-tenth of the wall thickness in a portion that adjoins the solid-state joint in a direction away from the aperture.

The solid-state joint can undo or reduce or prevent mechanical stresses that otherwise could result in destruction of the window component, for example in cooling of the housing after soldering-in of the window component, because of different thermal expansion coefficients of the materials of the housing and of the window component. Consequently the range of possible combinations of materials for the housing and of transparent materials for the window component is significantly expanded.

The minimum wall thickness of the housing is found, in particular, in the area of the solid-state joint.

The minimal wall thickness of the housing amounts, in particular, to at most 0.5 mm or at most 0.3 mm. In particular with stainless steel as the housing material, a minimum wall thickness of 0.2 mm in the area of the solid-state joint can be sufficiently robust with sufficient flexibility.

In a medical instrument as described here, the window component can comprise an amorphous material.

In particular, the window component can be made of glass. Especially by means of the solid-state joint and/or the thin-walled lip, the mechanical stress of the window component can be reduced to the point that amorphous materials can also be used for the window component with their mechanical properties that are in part markedly worse. Thus it is possible, for example, to dispense with birefringent sapphire. The broad range of optical properties of a number of glasses can make possible new uses of the medical instrument, for example new diagnostic methods.

A medical instrument as described here is, in particular, an endoscope, where the housing comprises a tube-shaped portion on whose end the aperture is positioned.

The tube-shaped portion is in particular positioned on the proximal end of the endoscope or forms the proximal end of the endoscope. The window component in this case is configured, for example, to uncouple light from the endoscope and is foreseen as a component of an eyepiece or for optical coupling with an eyepiece or a video camera. The described problematic nature of mechanical stresses, which are caused by various thermal expansion coefficients, is often particularly significant at the proximal end of an endoscope, because there the aperture and the window components are typically markedly greater than at the distal end of an endoscope.

In this method of producing a medical instrument, a housing is provided, an aperture and a thin-walled portion surrounding the aperture are configured, and a window component comprising a transparent material is inserted into the aperture.

In a method as described here, the thin-walled portion can be configured in such a way that it surrounds a lip so that the window component is inserted into the aperture in such a way that an edge of the lip is contiguous with an edge surface of the window component.

In a method as described here, the edge surface of the window component can be cohesively bound with the housing by means of soldering inside the lip.

In a method as described here, the edge surface of the window component can be cohesively bound by means of a cement outside the lip.

In a method as described here, the thin-walled portion can be configured in such a way that it includes a solid-state joint.

The methods described here are configured in particular to produce a medical instrument as described here.

BRIEF DESCRIPTION OF THE DRAWINGS

Embodiments are presented in further detail hereinafter with reference to the appended drawings, which are as follows.

DETAILED DESCRIPTION OF THE INVENTION

Figure 1:
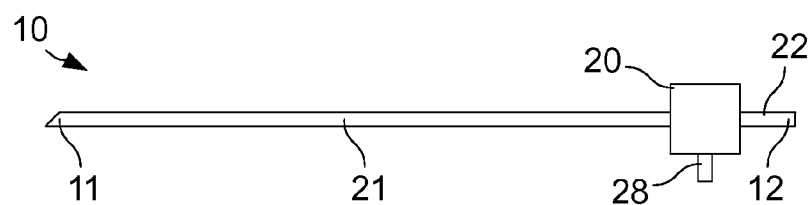
FIG. 1 shows a schematic depiction of an endoscope.

FIG. 1 shows a schematic depiction of an endoscope 10 with a distal end 11 and a proximal end 12. The endoscope 10 comprises a housing 20 with a long rigid or flexible shaft 21, which extends as far as the distal end 11 of the endoscope 10, and a tube-shaped portion 22 on the proximal end 12. In addition the endoscope 10 includes a junction 28 for a light conductor cable.

FIGS. 2 through 5 show schematic sectional depictions of various embodiments of the distal end 12 of the endoscope 10 from FIG. 1. The illustrated sectional planes each contain the longitudinal axis 14 of the endoscope or at least of the tube-shaped portion 22. In the case of a rotational symmetry of parts of the endoscope 10 (in particular of the shaft or tube-shaped portion 22 of the housing 20), the longitudinal axis 14 can simultaneously be the axis of symmetry.

Figure 2:
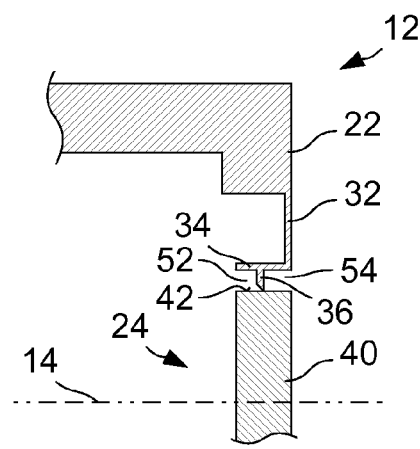
FIG. 2 shows a schematic depiction of an embodiment of the proximal end of the endoscope of FIG. 1.

FIG. 2 shows an embodiment of the proximal end 12 of the endoscope 10 in which the tube-shaped portion 22 of the housing 20 comprises a solid-state joint 32, a frame 34 and a lip 36. The solid-state joint 32, the frame 34 and the lip 36 are produced as a single piece with the tube-shaped portion 22 of the housing 20. The solid-state joint 32, the frame 34 and the lip 36 each surround the aperture 24 in ring-shaped manner. The solid-state joint 32, the frame 34 and the lip 36 each surround the aperture 24 in a circular ring shape when the aperture 24 is circular in shape.

A window component 40 is positioned in the aperture 24. Said window component 40 closes off the aperture 24. The lip 36 is contiguous with an edge surface 42 of the window component 40. A first groove 52 and a second groove 54 are bounded by the frame 34, the lip 36 and the edge surface 42 of the window component 40. Said first groove 52 and second groove 54 in the illustrated example each comprise an essentially rectangular cross-section and are separated from one another by the lip 36. In particular, the first groove 52 is provided for solder and the second groove 54 for cement.

If the window component 40 is circular in shape or if the edge surface 42 forms a segment of a cylindrical mantle, the solid-state joint 32 and the lip 36 in particular each essentially have the shape of a level and thin circular ring and the frame 34 essentially has the shape of a segment of a cylindrical mantle. In this case the grooves 52, 54 are also each of circular ring shape.

The wall thicknesses or material strengths of the solid-state joint 32, frame 34 and lip 36 are each clearly smaller than the wall thickness of the tube-shaped portion 22 of the housing 20 in other areas. The thicknesses of the solid-state joint 32 and lip 36 are each measured in the direction parallel to the longitudinal axis 14 of the endoscope 10, while the thickness of the frame 34 is measured radially or perpendicular to the longitudinal axis 14.

In particular, the thicknesses of the solid-state joint 32, frame 34 and lip 36 are each at most equal to one-fifth of the median wall thickness of the tube-shaped portion 22 of the housing 20 or to one-fifth of the area of the tube-shaped portion 22 of the housing 20 connecting in ring-shaped manner to the solid-state joint 32. For example, the thicknesses of the solid-state joint 32, frame 34 and lip 36 each are equal at most to 0.5 mm or at most to 0.3 mm or at most to 0.2 mm. Contrary to the depiction in FIG. 2, the thicknesses of the solid-state joint 32, frame 34 and lip 36 can differ from one another.

Contrary to the depiction in FIG. 2, the window component 40, instead of two level and plane-parallel border surfaces on the inside and on the outside of the housing, can comprise one or two surfaces that are domed in convex and/or concave manner. In this case the window component 40 can have the function of a diffuser lens or a convergent lens.

In particular, because of different thermal expansion coefficients of the materials of the tube-shaped portion 22 of the housing 20 on the one hand and of the window component 40 on the other hand, mechanical stresses can occur between the tube-shaped portion 22 of the housing 20 on the one hand and the window component 40 on the other hand, upon cooling after the soldering of the window component 40 into the aperture 24 as described below or upon autoclaving of the endoscope 10. Said mechanical stresses, however, can be partly relieved through the elasticity of the solid-state joint 32, frame 34 and lip 36. The mechanical strain on the window component 40 can thereby be reduced. This makes it possible to use glass as a material for the window component 40.

Figure 3:
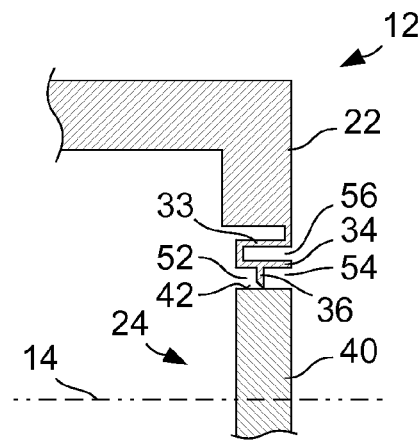
FIG. 3 shows a schematic depiction of an additional embodiment of the proximal end of the endoscope of FIG. 1.

FIG. 3 shows an embodiment of the proximal end 12 of the endoscope 10 that was presented above with reference to FIG. 1 and which resembles in some characteristics the embodiment presented above with reference to FIG. 2. Contrary to the embodiment presented above with reference to FIG. 2, the embodiment shown in FIG. 3 comprises a solid-state joint 33, which connects the frame 34, by an S-, Z- or N-shaped cross-section, with a more massive area of the tube-shaped portion 22 of the housing 20 that borders on the outside. In the illustrated example the solid-state joint 33 comprises a portion that forms a portion of a cylindrical mantle (with circular-shaped aperture 24: of a circular-cylindrical mantle) and is positioned coaxially to the frame 34. A third groove 56 borders on the cylindrical-mantle-shaped portion of the solid-state joint 33 and is open to the outside or to the surrounding of the housing 20.

In comparison to the solid-state joint 32 presented above with reference to FIG. 2, the solid-state joint 33 shown in FIG. 3 with a smaller structural space can have greater elasticity. The third groove 56 can be filled with cement or another material that is more elastic than the material of the housing 20 in order to prevent dirt from collecting in the third groove 56.

Figure 4:
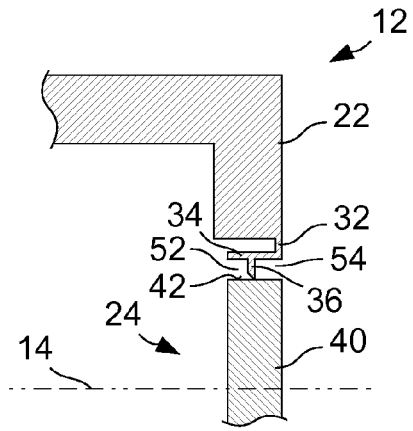
FIG. 4 shows a schematic depiction of an additional embodiment of the proximal end of the endoscope of FIG. 1.

FIG. 4 shows a schematic depiction of an additional embodiment of the proximal end 12 of the endoscope 10 presented above with reference to FIG. 1, which in some respects resembles the embodiments presented above with reference to FIGS. 2 and 3. The embodiment shown in FIG. 4 is distinguished from the embodiment presented above with reference to FIG. 2, especially through a substantially smaller radial extension of the circular-shaped level solid-state joint 32. In this case the portion of the frame 34 lying outside the lip 36 assumes the function of a solid-state joint to a significantly greater extent than in the embodiment presented above with reference to FIG. 2.

Figure 5:
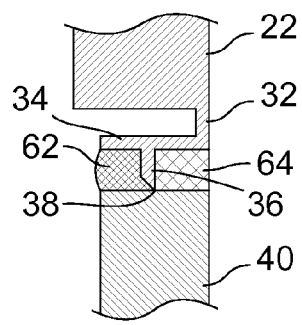
FIG. 5 shows an additional schematic depiction of the proximal end from FIG. 4.

Each of the embodiments shown above with reference to FIGS. 2 through 4 comprises a first groove 52, surrounding the window component 40, for soldering and a second groove 54, surrounding the window component 40, for cement. In FIGS. 2 through 4, the grooves 52, 54, however, still contain no solder or cement. FIG. 5 shows a schematic sectional depiction of an enlarged portion of the joint connection between the tube-shaped portion 22 of the housing 20 and the window component 40 in the example of the embodiment presented above with reference to FIG. 4. Corresponding joining connections are possible in the embodiments presented above with reference to FIGS. 2 and 3. It can also be recognized in FIG. 5 that the edge 38 of the lip 36 that is directed radially inward and borders on the edge surface 42 of the window component 40 can be configured as blade-shaped or with a wedge-shaped cross-section.

It can be recognized in FIG. 5 that solder 62 in the first groove 52 and cement 64 in the second groove 54 border respectively on the frame 34 and on the edge surface 42 of the window component 40. In particular, the solder 62 and cement 64 each form a cohesive bond between the frame 34 and the edge surface of the window component 40. The lip 36 separates the solder 62 and cement 64 from one another. Diffusion of components of the solder 62 into the cement 64 or vice versa is thereby strongly restricted. Mutual destruction is thereby prevented or at least delayed.

Both in the solder 62 and in the cement 64, the particular surface that is not simultaneously a border surface to the frame 34, lip 36 or window component 40 can in each case be convex (as shown in FIG. 5 for solder 62), flat (as shown in FIG. 5 for cement 64) or concave. The flat and flush configuration of the surface of the cement 64 with the outer surface of the tube-shaped portion 22 of the housing 20 and with the outer surface of the window component 40 has the advantage that no unclean edges are present in which impurities could accumulate.

A similar arrangement of a window component as is presented above with respect to FIGS. 1 through 5 for the proximal end 12 of the endoscope 10 is also possible on the distal end 11 and/or on the junction 28 for a light conductor cable.

Figure 6:
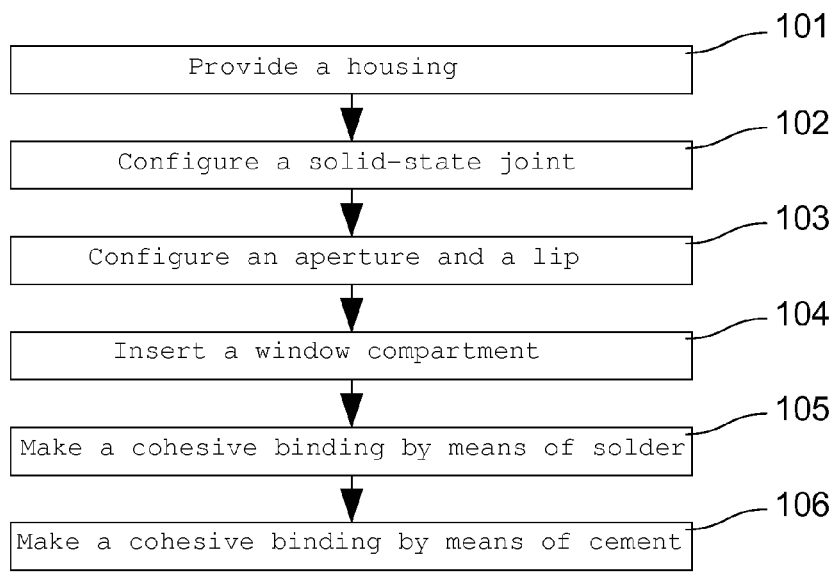
FIG. 6 shows a schematic flow diagram of a method for producing a medical instrument.

FIG. 6 shows a schematic flow diagram of a method for producing a medical instrument. Although it is possible by means of this method also to produce medical instruments that differ from the embodiments of an endoscope presented above with reference to FIGS. 1 through 5, hereinafter exemplary reference numbers from FIGS. 1 through 5 are used to facilitate understanding of the method.

In a first step 101, a housing 20 is provided. In a second step 102, a solid-state joint 32, 33 is configured on the housing. In a third step 103, an aperture 24 and a lip 36 are configured on the housing 20. The second step 102 and the third step 103 can be executed in reverse sequence or simultaneously. The aperture 24 and lip 36 can be configured in two different or separated steps.

In a fourth step 104, a window component 40 is inserted into the aperture 24 in the housing 20. In a fifth step 105, the window component 40 is cohesively bound by solder with the housing 20. In a sixth step 106, the window component 40 is cohesively bound by cement with the housing 20. The fifth step 105 and sixth step 106 can be executed in reverse sequence or simultaneously.

What is claimed is:

1. A medical instrument comprising:
    a housing comprising an elongate tubular body with an aperture disposed at a proximal end of the elongate tubular body;
    a window component, which comprises a transparent material and closes off the aperture;
    a thin-walled portion of the housing, which surrounds the aperture, the thin-walled portion including a solid-state joint, a frame and a lip;
    the lip contacts an outer circumferential edge of the window component;
    a first groove positioned proximal to the lip and bound by the frame, the lip and the outer circumferential edge surface of the window component;
    a second groove positioned distal to the lip and bound by the frame, the lip and the outer circumferential edge surface of the window component; and
    wherein the solid-state joint, the frame and the lip each have a thickness less than a thickness of the elongate tubular body of the housing.

2. The medical instrument of claim 1, further comprising a soldering disposed in one of either the first groove or the second groove, the soldering cohesively binding the frame around the aperture and the outer circumferential edge surface of the window component.

3. The medical instrument of claim 2, further comprising a cement disposed in one of either the first groove or the second groove, the cement cohesively binding the frame around the aperture and the outer circumferential edge surface of the window component.

4. The medical instrument of claim 1, wherein a minimum wall thickness of the housing is found in an area of the solid-state joint.

5. The medical instrument of claim 1, wherein the window component comprises an amorphous material.

6. The medical instrument of claim 1, wherein the medical instrument is an endoscope.

7. A method for producing a medical instrument, wherein the following steps are performed:
    providing a housing comprising an elongate tubular body;
    configuring an aperture at a proximal end of the elongate tubular body and a thin-walled portion of the housing that surrounds the aperture into the housing, the thin-walled portion configured in such a way that it includes a solid-state joint, a frame and a lip;
    inserting a window component, which comprises a transparent material, into the aperture such that the lip contacts an outer circumferential edge of the window component and closes off the aperture,
    providing a first groove proximal to the lip bounded by the frame, the lip and the outer circumferential edge surface of the window component;
    providing a second groove distal to the lip and bounded by the frame, the lip and the outer circumferential edge surface of the window component; and
    wherein the solid-state joint, the frame and the lip each have a thickness less than a thickness of the elongate tubular body of the housing.

8. The method of claim 7, in addition with at least one of the following steps:
    making a cohesive binding of the edge surface of the window component with the housing by means of solder, where the solder is disposed adjacent and distal to the lip; and
    making a cohesive binding of the edge surface of the window component with the housing by means of a cement, where the cement binding the frame around the aperture and the edge surface of the window component.

9. The medical instrument of claim 6, wherein the solid-state joint, and the lip are produced as a single piece with the tube-shaped portion of the housing.

10. The medical instrument of claim 1, wherein the solid-state joint, the frame and the lip each surround the aperture in ring-shaped manner.

11. The medical instrument of claim 10, wherein the aperture is circular in shape.

12. The medical instrument of claim 1, wherein the first groove and the second groove comprise an essentially rectangular cross-section and are separate from one another by the lip.

13. The medical instrument of claim 1, wherein the window component is circular in shape.

14. The medical instrument of claim 1, wherein the window component has one or two surfaces that are domed in convex and/or concave manner.

15. The medical instrument of claim 1, wherein the solid-state joint connects to the frame by an S-, Z- or N-shaped cross section.

16. The medical instrument of claim 1, wherein the thickness of the solid-state joint, the frame and the lip are each at most equal to one-fifth of the median wall thickness of the tube-shaped portion of the housing.

17. A medical instrument comprising:
    a housing having an aperture;
    a window component, which comprises a transparent material and closes off the aperture;
    a thin-walled portion of the housing, which surrounds the aperture, the thin-walled portion including a solid-state joint, a frame and a lip, the window component held in place by only the lip, the lip contiguous with an outer perimeter edge surface of the window component;

a first groove positioned on a first side of the lip and bound by the frame, the lip and the outer perimeter edge surface of the window component;
a second groove positioned on a second side of the lip and bound by the frame, the lip and the outer perimeter edge surface of the window component;
the first groove and the second groove being separated by the lip; and
wherein the housing, the lip, the frame and the solid-state joint are formed of a single piece, wherein the lip, the frame and the solid-state joint extend inward from the housing toward the window component.

18. An endoscope comprising:
a housing comprising an elongate tubular body with an aperture disposed at a proximal end of the elongate tubular body;
an amorphous window component, which comprises a transparent material and closes off the aperture;
a thin-walled portion of the housing, which surrounds the aperture, the thin-walled portion including a solid-state joint, a frame and a lip, the lip contacting an outer circumferential edge of the window component;
a first groove positioned proximal to the lip and bound by the frame, the lip and the outer circumferential edge of the window component;
a second groove positioned distal to the lip and bound by the frame, the lip and the outer circumferential edge of the window component; and
wherein the solid-state joint, the frame and the lip each have a thickness less than a thickness of the elongate tubular body of the housing.

* * * * *